United States Patent [19]

Kihira et al.

[11] Patent Number: 5,580,788
[45] Date of Patent: Dec. 3, 1996

[54] USE OF IMMUNOGLOGULIN-BINDING ARTIFICIAL PROTEINS AS MOLECULAR WEIGHT MARKERS

[75] Inventors: Yasunori Kihira; Sachiko Aiba, both of Shiga-ken, Japan

[73] Assignee: Oriental Yeast Co., Ltd., Tokyo, Japan

[21] Appl. No.: 406,809

[22] Filed: Mar. 20, 1995

Related U.S. Application Data

[63] Continuation of Ser. No. 30,477, filed as PCT/JP92/00938, Jul. 23, 1992 published as WO93/02107, Feb. 4, 1993, abandoned.

[30] Foreign Application Priority Data

Jul. 25, 1991 [JP] Japan ................................. 3-207150
Aug. 23, 1991 [JP] Japan ................................. 3-235687

[51] Int. Cl.$^6$ ..................... G01N 33/68; G01N 33/544
[52] U.S. Cl. ..................... 436/15; 436/528; 530/350; 435/69.1
[58] Field of Search ..................... 530/350, 402; 435/69.1, 7.6, 7.9; 436/15, 528

[56] References Cited

U.S. PATENT DOCUMENTS

| | | | |
|---|---|---|---|
| 4,507,233 | 3/1985 | Saito et al. | 530/363 |
| 4,894,436 | 1/1990 | Auerswald et al. | 530/324 |

FOREIGN PATENT DOCUMENTS

| | | |
|---|---|---|
| 0107509 | 10/1983 | European Pat. Off. . |
| 0225860 | 12/1986 | European Pat. Off. . |
| 0284368 | 3/1988 | European Pat. Off. . |
| 59-50163 | 10/1984 | Japan . |
| 64-60388 | 3/1989 | Japan . |

OTHER PUBLICATIONS

Strandberg, L., et al. (1990) J. Biotechnol. 13:83–96.
Mori, T., et al. (1989) Chem. Abs. 112(9):71653g [English Summary of JP 01060388].
Ljungberg, U. K., et al. (1993) Mol. Immunol. 30:1279–85.
M. Uhlen et al.: "Complete sequence of the Staphylococcal Gene Encoding Protein A", Journal of Biological Chemistry, vol. 259, No. 3, (1984), pp. 1695–1702.
B. Nilsson et al.; "A synthetic IgG–binding Domain Based On Staphylococcal Protein A", Protein Engineering, vol. 1, No. 2, 1987, pp. 107–113.
A. Saito et al.; "High Level Expression Of A Stynthetic Gene Coding for Ig–Biding Domain B of Staphylococcal Protein A", Protein Engineering, vol. 2, No. 6, 1989, pp. 481–487.
Saburo Mitsui et al.; "Dictionary of Biotechnology", CMC Inc. 1986–10–9, p. 958.

*Primary Examiner*—David L. Fitzgerald
*Attorney, Agent, or Firm*—Browdy and Neimark

[57] ABSTRACT

The present invention relates to immunoglobulin-binding artificial proteins (repetitively linked-proteins) which result when either one of or several numbers of the IgG-binding domains in protein A molecule is defined as a unit, and repetitive multiple links are made thereof. These repetitive proteins exhibit a superior ability for IgG purification to naturally occurring protein A, and the mixture of these repetitive proteins may be used as excellent molecular weight markers.

10 Claims, 7 Drawing Sheets

FIG. 1

E  AlaGlnHisAspGluAlaGlnAsnAlaPheTyrGlnValLeuAsn
D  AlaAspAlaGlnGlyAsnAsnPheAsnLysAspGlnSerAlaPheTyrGluIleLeuAsn
A      AlaAspAsnAsnPheAsnLysGluGlnAsnAlaPheTyrGluIleLeuAsn
B      AlaAspAsnLysPheAsnLysGluGlnAsnAlaPheTyrGluIleLeuHis
C      AlaAspAsnLysPheAsnLysGlyGlnAsnAlaPheTyrGluIleLeuHis

E  MetProAsnLeuAsnAlaAspGlnArgAsnGlyPheIleGlnSerLeuLysAspAspProSer
D  MetProAsnLeuAsnGluAlaAspGlnArgAsnGlyPheIleGlnSerLeuLysAspAspProSer
A  MetProAsnLeuAsnGluGluGlnArgAsnGlyPheIleGlnSerLeuLysAspAspProSer
B  LeuProAsnLeuAsnGluGluGlnArgAsnGlyPheIleGlnSerLeuLysAspAspProSer
C  LeuProAsnLeuThrGluGlnArgAsnGlyPheIleGlnSerLeuLysAspAspProSer

E  GlnSerAlaAsnValLeuGlyGluAlaGlnLysLeuAsnAspSerGlnAlaProLys
D  GlnSerThrAsnValLeuGlyGluAlaLysLysLeuAsnGluSerGlnAlaProLys
A  GlnSerAlaAsnLeuLeuSerGluAlaLysLysLeuAsnGluSerGlnAlaProLys
B  GlnSerAlaAsnLeuLeuGluAlaLeuLysLeuAsnAspAlaGlnAlaProLys
C  ValSerLysGluIleLeuGluAlaLeuGluAlaLysLeuAsnAspAlaGlnAlaProLys

PROTS:
```
         AccI
          ↓
(5')-GGTAGACGCTGATAACAATTTCAACAAA-(3')              28-mer
     ValAspAlaAspAsnAsnPheAsnLys
        λN-terminus  C-terminus
```

PROTAS:
```
                              AsnAspAlaGlnAlaProLys
(3')-ATTTACTACGAGTTCGTGGTTTTCATCTGG-(5')            30-mer
                                    λ
                                   AccI
```

ACCS:
```
     EcoRI    AccI  pTZ19U
       ↓       ↓
(5')-GGAATTCATGAAAGTAGACACTGGCCGTCGTTTTACAA-(3')    38-mer
     MetLysValAsp
```

ACCAS:
```
(3')-TGCATTTTTCCCATCTTAAGG-(5')                     21-mer
                       λ
                      EcoRI
```

USE OF IMMUNOGLOGULIN-BINDING ARTIFICIAL PROTEINS AS MOLECULAR WEIGHT MARKERS

This application is a continuation of U.S. application Ser. No. 08/030,477, now abandoned, which was filed as International Application PCT/JP92/00938 on 23 Jul. 1992 and which entered the U.S. national phase under 35 U.S.C. § 371(c) on 24 Mar. 1993, published as WO93/02107, Feb. 4, 1993.

FIELD OF THE INVENTION

The present invention relates to a group of immunoglobulin-binding artificial proteins, whose immunoglobulin G (IgG)-binding ability is higher than that of protein A, a naturally occurring IgG-binding protein. These artificial IgG-binding proteins themselves are useful as an excellent molecular weight marker, and may be used in a wide range of biotechnological fields.

TECHNIQUES AND DISADVANTAGES OF THE PRIOR ART

It is already known that protein A is a cell wall protein of *Staphylococcus aureus,* and can be isolated from culture media of Cowan I strain ("Dictionary of Biotechnology", supervised by Saburo Mitsui, et al., CMC, Inc., p.958, 1986-10-9). There are two examples of repetitive artificial proteins similar to the proteins described in the present invention, which are synthesized by genetic engineering techniques with repeating the gene of one of IgG-binding domain of protein A. One is repetitive artificial proteins of mutant domain Z by Nilsson, et al. (Protein Engineering 1, 107–113, 1987) and the other is repetitive artificial proteins of domain B by Saito, et al. (Protein Engineering 2, 481–487, 1989). In the present invention the relationship between the IgG-binding ability of the repetitive artificial proteins and their repetition number are examined in detail.

In addition, several marker proteins for SDS-polyacrylamide gel electrophoresis are known in the prior art; for example, some already-known molecular weight marker proteins used for SDS-polyacrylamide gel electrophoresis include mixtures of proteins of appropriate molecular weights, such as myosin (H-chain), β-galactosidase, phosphorylase b, bovine serum albumin, ovalbumin, carbonic anhydrase, soybean trypsin inhibitor, lysozyme, etc. In the prior art, a portion of the membrane containing the marker protein which are transferred from the gel is needed to be cut off in order to be stained with a dye such as Amido Black, etc. Pre-stained markers covalently bound to appropriate dyes are visible during electrophoresis, and these are transferred on the membrane. Further, the molecular weight markers for western blotting are obtainable by biotinization of the above mentioned proteins and by subsequent reaction with avidin-horseradish peroxidase (HRP) conjugate, followed by color development (biotin-labelled markers).

However, the marker proteins used according to the prior art are mixtures of different kinds of proteins, and thus the stainability and stability of each of the bands vary widely, with some bands in particular fading during storage. The pre-stained markers show a change in mobility due to binding with the dye, while the exact molecular weight does not match the estimated value, and the bands are generally broad. The biotin-labelled markers require avidin-HRP, which is not generally acceptable.

Most of the marker proteins which have been used in the prior art have non-uniform molecular weights, which not only reduce precision but also make it impossible to make modifications in the molecular weight and to freely and efficiently produce the object marker protein.

MEANS TO SOLVE THE POINTS AT ISSUE

In the present invention, the gene of domains A and B of the IgG-binding domains of protein A molecule may be freely amplified using the PCR method (primer-utilizing gene amplification method), making possible for the first time the easy production of repetitive artificial proteins having IgG-binding ability.

Among the repetitive artificial proteins obtained in this manner (referred to as simply "repetitive proteins" hereunder), some proteins exhibited, quite unexpectedly, an ability to bind specifically to IgG which was higher than that of naturally occurring protein A, and it was the result of further research based on this finding that led to completion of the present invention.

Regarding the molecular weight marker, the gene of domains A and B of the IgG-binding domain of protein A was freely amplified using the PCR method, resulting in success for the first time to produce repetitive proteins having IgG-binding ability by linking these domains.

BRIEF DESCRIPTION OF FIGURES

FIG. 8 is drawn a diagram of a molecular weight marker proteins prepared according to the present invention. Those marker proteins were subjected to SDS-polyacrylamide gel electrophoresis followed by electroblotting on polyvinylidene difluoride membrane. The marker proteins were bound with the primary antibody, rabbit antibody, and then the secondary antibody, goat anti-rabbit antibody conjugated with HRP. The protein bands were visualized by the HRP reaction with color development using 4-chloro-1-naphthol. The lanes in FIGS. 7 and 8 represent the following: lane M, molecular weight marker of BRL Co.; 1, PROT-ABI; 2, PROT-ABII; 3, PROT-ABIII; 4, PROT-ABIV; 5, PROT-ABV; 6, PROT-ABVI; 7, 8, 9, 10, mixtures of lanes 1–6. For the CBBR staining, 10 μg each of PROT-ABI, II and 0.5 μg each of PROT-ABIII to VI were used for the blotting, 0.1 μg each of PROT-ABI, II and 0.05 μg each of PROT-ABIII to VI were used for lanes 1–7, 0.5 μg each of PROT-ABI, II and 0.25 μg each of PROT-ABIII to VI were used for lanes 8 and 9, and 1.0 μg each of PROT-ABI, II and 0.5 μg each of PROT-ABIII to VI were used for lane 10.

As will be made clear from the following description, repetitive proteins in the present invention may be easily prepared as a set of substances with a desired molecular weight by a gene technology, and amazingly excel in their ability to bind IgG specifically. Therefore, the repetitive proteins in the present invention are able to selectively bind IgG in an IgG-containing sample, and thus can be used to purify and separate IgG. Likewise, they may be used in the opposite manner to selectively eliminate IgG from said sample. In addition, though this repetitive proteins have an excellent ability to bind IgG, the bound IgG can be easily eluted with an appropriate eluent.

Either a heterogeneous or a homogeneous system may be used to purify IgG using the repetitive proteins prepared according to the present invention, and any suitable conventional method may be employed in either case.

For example, if a heterogeneous system is used, then the repetitive proteins prepared according to the present invention may be immobilized on a container, the wall of a container or a carrier using any conventional method, and an IgG-containing sample may be contacted with the proteins using either a batch method or a continuous method. The method for immobilization may be a method suitable for immobilizing microorganisms and enzymes, preferably one of the various types of carrier-binding methods such as the covalent bond method, the ionic bond method or the physical adsorption method. Also, the material chosen for the carrier or the wall of the container may be that which is most suitable for the binding method used, with a wide range of choices available, for example, synthesized or natural organic substances such as synthesized resins, polysaccharides, etc.; inorganic substances such as glass, metal, porous clay, etc.; biological substances such as blood cells, cells, microorganic cells, etc.

The carrier which thus immobilizes the repetitive proteins prepared according to the present invention is, for example, filled into a column, after which an IgG-containing sample is put into the column to cause only the IgG to selectively bind to the immobilizing carrier. Then, when an elution is drawn therefrom the IgG is eluted out, and thus purified IgG may be obtained in a continuous manner. Moreover, this procedure may be repeated in order to achieve a higher degree of purity, and as the need arises retreatment may be done using a newly prepared column filled with said protein A immobilizing carrier. Likewise, when using a batch method, purification may be done by binding of IgG to the carrier in the same manner, separation of solid and liquid, and finally elution of IgG.

EXAMPLE 1

(1) Construction of plasmids pTRP-PROT-ABI to VI

Figure 2:
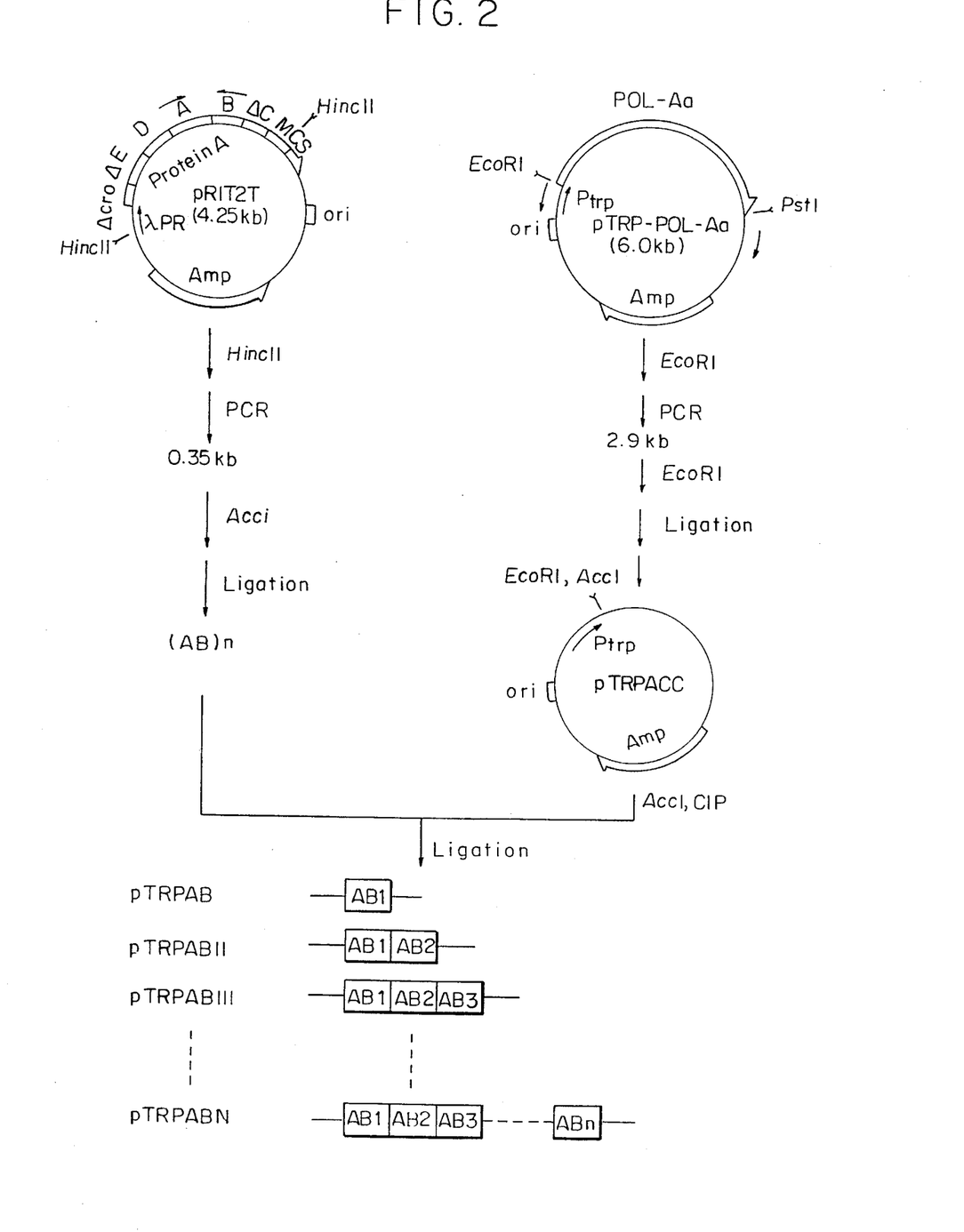
FIG. 2 is a schematic strategy of construction of an expression plasmid used in the present invention.

The AB domain of protein A was selected as a unit part of the repetitive proteins, and its gene was synthesized by the PCR method using commercially available protein A-fusion protein-expression vector pRIT2T as the template (FIG. 2). Here, a sequence recognized by restriction enzyme AccI was introduced to both termini of the gene, to cause the gene to be linked in a head-to-tail manner. The sequence recognized by AccI is non-palindromic, and thus the DNA fragment which contains such a sequence on both termini is characteristically only linked in a fixed direction. There are some other such restriction enzymes, for example, AflIII, AvaI, BanI, BanII, HgiAI, etc.

Figure 3:
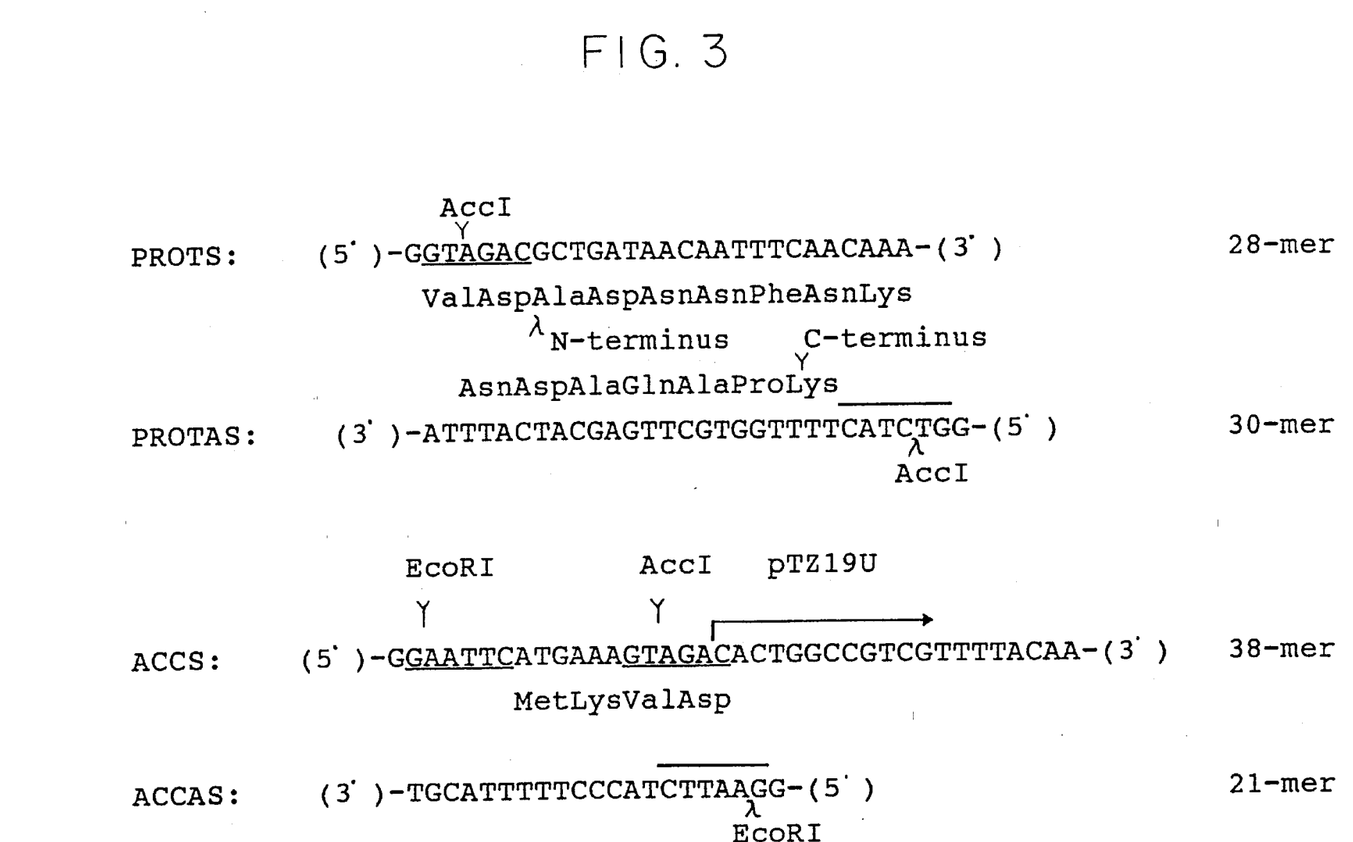
FIG. 3 shows the nucleotide sequences for the two types of primers (PROTS, SEQ ID NO:6, PROTAS, SEQ ID NO:7) necessary for amplification of the gene of the AB domain of protein A using the PCR method, and for the two types of primers (ACCS, SEQ ID NO:8, ACCAS, SEQ ID NO:9) necessary for introduction of the initiation codon and the AccI site into the expression vector.

A so-called ATG vector (pTRPACC) with a trp promoter was prepared as the expression vector, which carries an AccI site as the cloning site, and initiation codon ATG followed by lysine codon AAA in order to achieve a highly efficient expression in E. coli. The above mentioned gene fragment of the AB domain of the protein A was polymerized one to six times and inserted into the expression vector. In the PCR reaction, a pRIT2T cut off with HincII was used as the template, while 5'-GGTAGACGCTGATAACAATTTCAA-CAAA-3' (FIG. 3, PROTS, SEQ ID NO:6) was used as a sense primer and 5'-GGTCTACTTTTGGTGCTTGAGCAT-CATTTA-3' (FIG. 3, PROTAS, SEQ ID NO:7) was used as an antisense primer. Here, the gene for the target AB domain was amplified with Taq polymerase (2.5 units); the condition of PCR was 30 cycles of 94° C. for 1 minute, 50° C. for 1 minute and 72° C. for 5 minutes. The expression vector was also synthesized by a PCR method in the same manner using the sense primer (ACCS) and antisense primer (ACCAS) shown in FIG. 3 to introduce an initiation and lysine codons, and AccI site for insertion of the polymerized gene fragments.

The ligation reaction was conducted at 14° C. for 16 hours, using T4DNA ligase (350 units). The product of this reaction was then used for transformation of E. coli JM109 (recA1, endA1, gyrA96, thi, hsdR17, supE44, relA1, λ-, Δ(lac-ProAB), [F', traD36, proAB, lacI9, lacZΔ M15 ]), and the cells were then mixed with an agar culture medium (composition: 10 g of trypton, 5 g of yeast extracts and 10 g of sodium chloride per liter; pH 7.4) containing 0.7% agar and 100 μg/ml of ampicillin. These cells were then laid on the plate of an L-agar culture medium containing 1.5% agar and 100 μg/ml of ampicillin, and cultured overnight at 37° C. The plasmid DNA of the transformant was then isolated using the alkali-SDS method, after which agarose gel electrophoresis was conducted and the clone with the target DNA fragment inserted therein was selected. The obtained plasmid DNA was partially digested by AccI to determine how many units of the gene of the AB domain of protein A had been inserted, and the plasmids containing fragments of one unit to six units were named pTRP-PROT-ABI to pTRP-PROT-ABVI, respectively.

The pTRP-PROT-ABIV-transformed E. coli is deposited at the Fermentation Research Institute, Agency of Industrial Science and Technology in Japan as FERM BP-3930, under the identification of Escherichia coli JM109/pTRP-PROT-AB4.

(2) Culturing of transformed E. coli JM109/pTRP-PROT-ABI to VI

E. coli which were transformed with plasmids pTRP-PROT-ABI to VI were cultured in an LB culture medium containing 100 μg/ml of ampicillin, at 37° C. for 24 hours. The cells thus obtained were stored at −20° C.

(3) Disruption of the cells and purification of each marker protein

The frozen cells were thawed at room temperature, after which they were suspended in a 50 mM phosphate buffer solution (pH 7.5) containing 0.1 mM EDTA and 0.15M NaCl, the volume of which was 3 times the cells, and the cells were disrupted with a Dyno-Mill. To this was added 1/50 volume of 10% Lubrol PX and stirring was done at 0° C. for 15 minutes followed by centrifugation at 15,000 rpm for 20 minutes at 4° C. The supernatant thereof was 30% saturated with ammonium sulfate, and was subjected to centrifugation. This supernatant was then 60% saturated with ammonium sulfate and then subjected again to centrifugation to obtain 30–60% saturated ammonium sulfate precipitation fractions. They were then dissolved in a small amount of buffer solution A (a 50 mM phosphate buffer solution containing 0.1 mM EDTA, pH 7.5), and after desalting with a Sephadex G-25 column it was applied to a DEAE-Sepharose column which had been equilibrated with buffer solution A. The object protein adsorbed on the DEAE-Sepharose column under these conditions. The column was then adequately washed with buffer solution A, after which elution was done using buffer solution A with a linear concentration gradient of 0–1M NaCl. The object protein was detected by ELISA using HRP-conjugated goat anti-rabbit IgG antibody. The object protein fractions were then applied to an IgG-Sepharose column which had been equilibrated with a 50 mM Tris-HCl buffer solution, pH 7.4, containing 0.15M NaCl and 0.05% Tween 20. After adequately washing the column with the same buffer solution, elution was done using a 0.5M ammonium acetate buffer solution (pH 3.4). The eluted fractions were then precipitated with 80% saturated ammonium sulfate, and the precipitate was dissolved in a small amount of buffer solution A, after which the resulting solution was subjected to high-performance molecular sieve chromatography on a TSKgel G3000SW column which had been equilibrated with a 0.1M phosphate buffer solution, pH 7.0, containing 0.2M NaCl. Thus obtained fractions produced a single band in SDS-polyacrylamide gel electrophoresis. Table 1 below lists the number of repeat of the AB domain of each repetitive protein along with its molecular weight. One AB domain is composed of 116 amino acids, and its molecular weight is 13,205.24. There are four amino acids, MetLysValAsp, SEQ ID NO:10, attached to the N-terminus of each repetitive protein, and eight amino acids, ThrGlyArgArgPheThrThrSer, SEQ ID NO:1, attached to the C-terminus thereof. In addition, each AB domain is linked with two amino acids, ValAsp.

TABLE 1

Number of links of the AB domain of each marker protein and its molecular weight.

| Marker protein | AB domain No. | Molecular weight |
| --- | --- | --- |
| PROT-ABI | 1 | 14,586 |
| PROT-ABII | 2 | 27,987 |
| PROT-ABIII | 3 | 41,389 |
| PROT-ABIV | 4 | 54,790 |
| PROT-ABV | 5 | 68,192 |
| PROT-ABVI | 6 | 81,593 |

Structure of marker protein: NH2-MKVD-(AB domain-VD)N-TGRRFTTS-COOH
n = number of repeat of AB domain

EXAMPLE 2

(1) Preparation of immobilizing carrier

In a column, 0.3 g of a carrier (cyanogen bromide activated Separose 4B: Pharmacia Co.) was swelled with 1 mM HCl for 15 minutes. The swollen gel was then washed with 1 mM HCl (200 ml per 1 g of dried gel). It was further washed with a coupling buffer (0.1M of $NaHCO_3$ (pH 8.3)–0.5M NaCl) (5 ml per 1 g of dried gel). Separately, a ligand protein (the repetitive proteins prepared in Example 1: one to six times repeated AB domains (i.e., PROT ABI-VI) were dissolved in a coupling buffer. Commercially available native protein A was also dissolved in the same buffer for control ligand solution. The solutions were each mixed with the above mentioned gel at a proportion of 2 ml of ligand solution to 1 ml of gel, and the suspensions were shaken overnight at 4° C. After the ligand solution was eliminated, a blocking reagent (0.2M glycine, pH 8.0) was then added thereto and the suspensions were kept at room temperature for 2 hours. The resulting gels were washed with the coupling buffer, 0.1M acetate buffer (pH 4.0)–0.5M NaCl, and again with the coupling buffer in this order. Seven kinds of columns were prepared filled with the carrier immobilizing each repetitive proteins and protein A. Excellent binding efficiency to carriers was observed in every ligand protein; for example, the binding efficiency of PROT-ABIV with its carrier was about 95%.

(2) Isolation and purification of IgG

Figure 4:
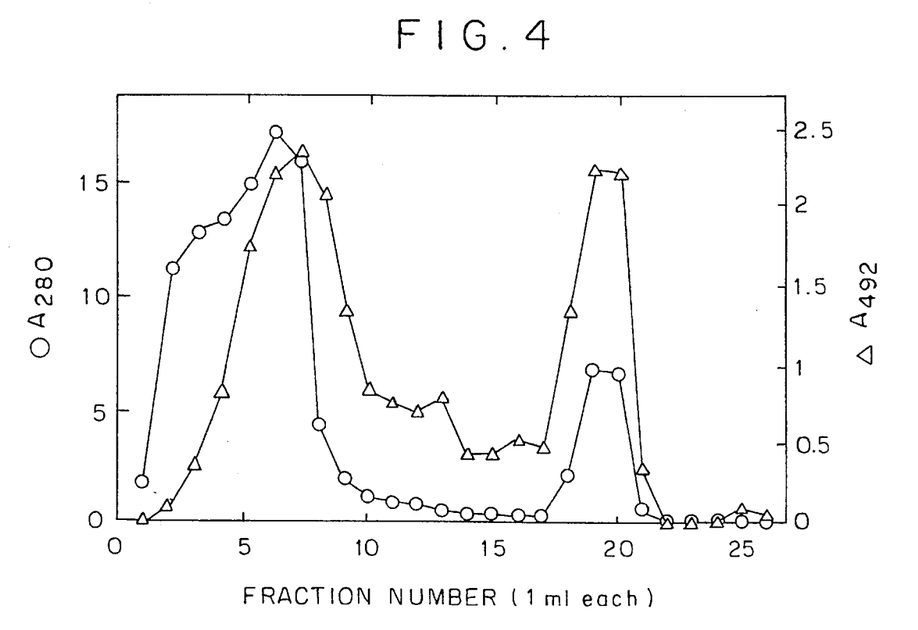
FIG. 4 is an affinity chromatogram of rabbit antibody on a PROT-AVIV-Sepharose column (○ protein, △: IgG).

Two ml of rabbit serum was diluted by adding 4 ml of buffer B [0.1M sodium phosphate (Na-Pi), pH 7.0], and filtrated. It was then applied on each of the columns prepared as described above. Each column was washed with 10 ml of buffer C. Bound IgG was eluted with buffer B (0.3M KCl-HCl, pH 2.3). Eluate was collected at 1 ml each of fractions. The protein and IgG amounts were measured with absorbance at 280 nm ($A_{280}$) and by the ELISA method with absorbance at 492 nm ($A_{492}$) respectively. From these results, the amount of IgG which adsorbed to 1 ml of each immobilizing carrier and eluted out was calculated, thereby providing the value as the binding capacity. The result of affinity chromatography for PROT-ABIV is shown in FIG. 4, which clearly indicates that IgG is eluted mainly in fractions Nos. 19 and 20.

Figure 5:
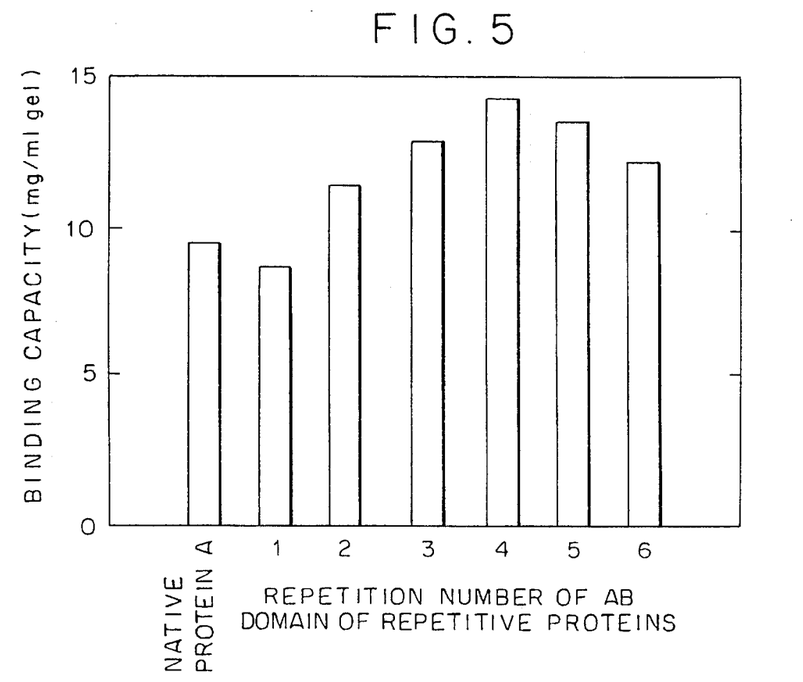
FIG. 5 shows the binding capacity of six types of recombinant protein A for IgG from rabbit antiserum.
Figure 6:
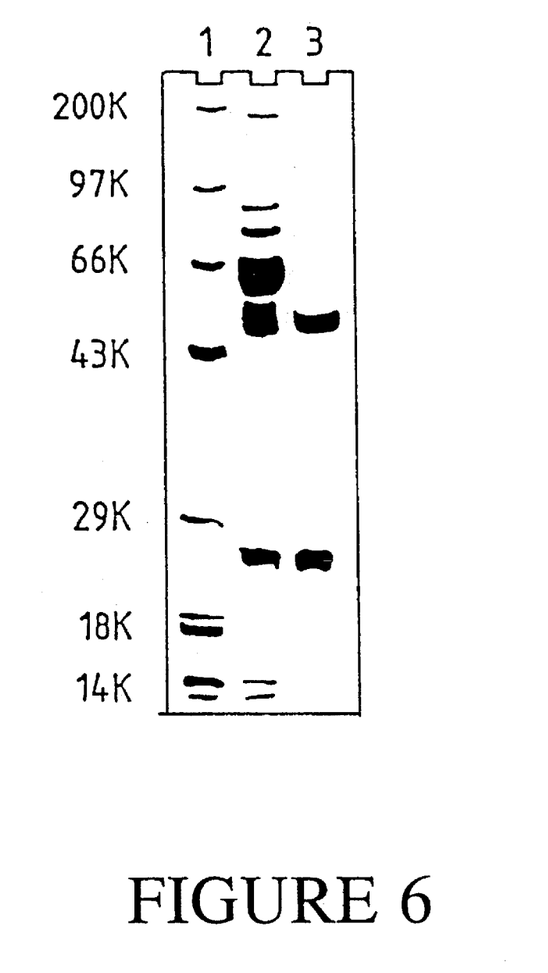
FIG. 6 is a drawing of an SDS-polyacrylamide gel electrophoretic pattern of rabbit IgG purified using a PROT-AVIV-Sepharose column. (1: molecular weight marker, 2: rabbit antiserum, 3: purified IgG).

The results of measurement of the binding capacity of each repetitive proteins and commercially available native protein A for IgG are shown in FIG. 5. As these results make clear, the binding capacity of the repetitive proteins for IgG increased in proportion with the increase in the number of repeat of the IgG-binding domain; for example, the binding capacity of PROT-ABIV was about 35% greater than that of protein A. Also, when 4 µg of the rabbit IgG which was purified with the PROT-ABIV-Sepharose column was applied to SDS polyacrylamide gel electrophoresis, the pattern shown in FIG. 6 was obtained. In this figure, lane 1 represents a commercially available molecular weight marker, lane 2 represents rabbit serum (8 µg), and lane 3 represents purified IgG (4 µg). The results shown in FIG. 6 clearly substantiate the fact that the object IgG was concentrated and purified to a very high degree.

EXAMPLE 3

Various repetitive proteins were prepared in the same manner as in Example 1, but using the D domain of protein A. The results are shown in Table 2 below. Table 2 lists the number of repeat of D domain and the molecular weight of each repetitive protein.

TABLE 2

Molecular weight of each marker protein when the D domain is a repeating unit.

| Marker protein | D domain No. | Molecular weight |
| --- | --- | --- |
| PROT-$D_1$ | 1 | 8,220 |
| PROT-$D_2$ | 2 | 15,256 |
| PROT-$D_3$ | 3 | 22,291 |
| PROT-$D_4$ | 4 | 29,327 |
| PROT-$D_5$ | 5 | 36,362 |

Structure of marker protein: $NH_2$-MKVD-(D domain-VD)n-TGRRFTTS-COOH
n = number of repeat of D domain Each of these repetitive proteins also exhibited an excellent ability to purify IgG, as in the case of Example 2 relating to the AB domain.

Figure 1:
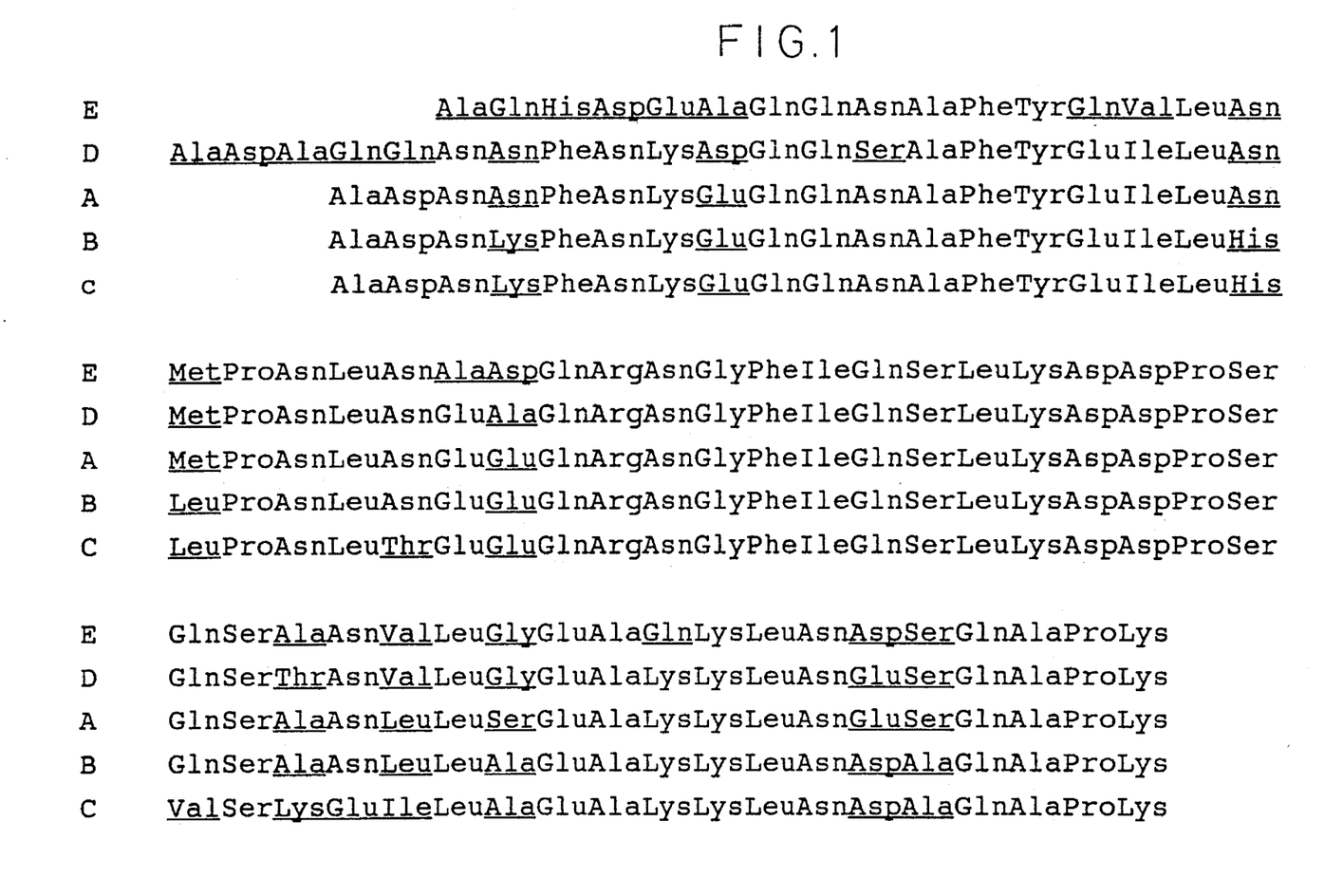
FIG. 1 shows a homology in the amino acid sequences of the five IgG-binding domains (E, D, A, B, C) of protein A molecule. These sequences are displayed as, SEQ ID NO:11 and 2–5 respectively. The amino acids are underlined in the portions below three mathes among the five domains.

As the above results clearly show, each of the repetitve proteins according to the present invention, with varying molecular weights, can be easily produced as desired. Protein A also has IgG-binding domains, E and C (whose amino acid sequences are listed in FIG. 1), in addition to the above mentioned domains A, B and D. Thus, the same methods mentioned above may be used in the case of domains E and C as well, to easily produce the desired repetitive proteins between identical or different domains, and thus obtained repetitive proteins may be used to purify IgG to a high degree.

EXAMPLE 4

Figure 7:
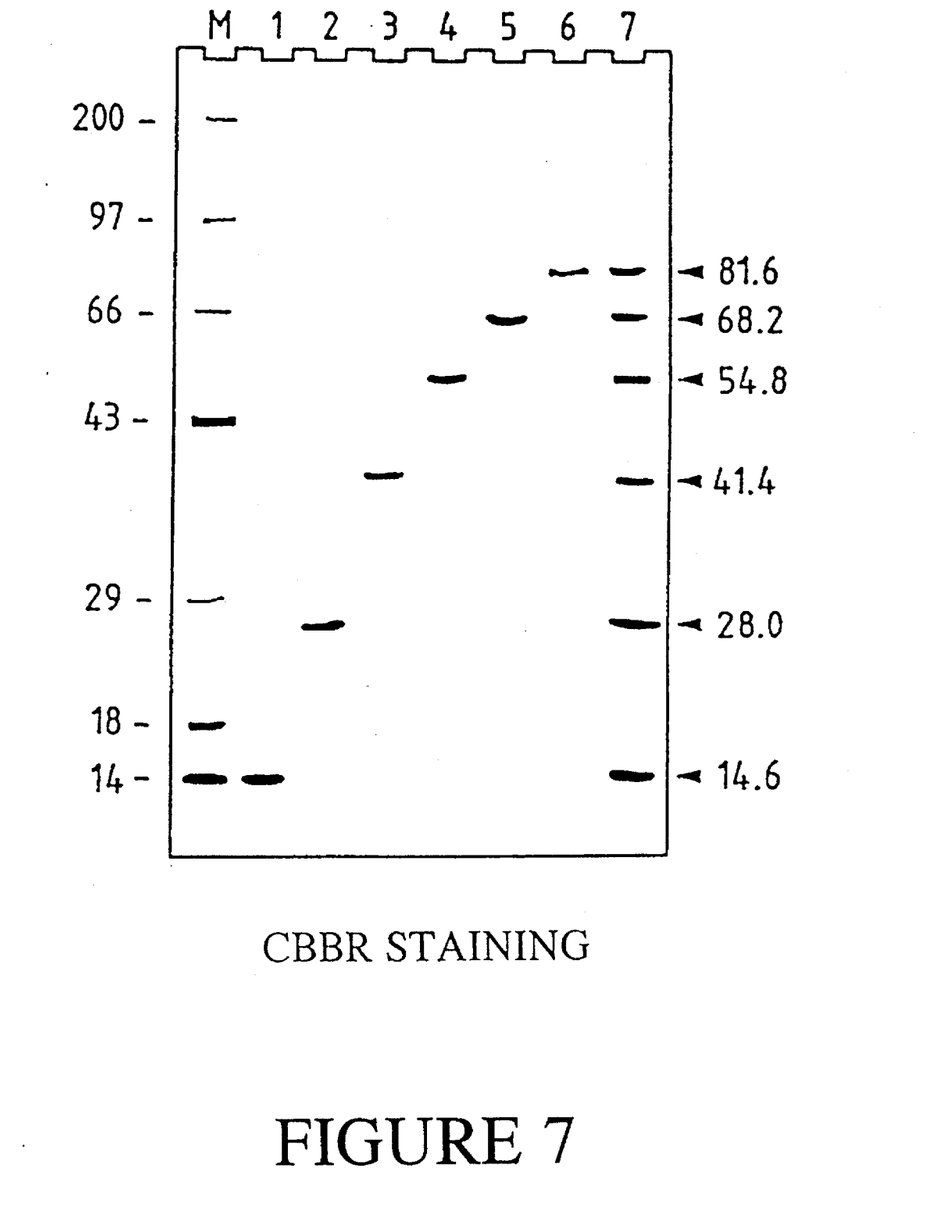
FIG. 7 is a drawing of an SDS-polyacrylamide gel electrophoretic pattern of molecular weight marker proteins prepared according to the present invention. The gel was stained with coomassie brilliant blue R-250.

The six types of marker proteins produced in Example 1 were subjected to SDS-polyacrylamide gel electrophoresis, and the gel was stained with coomassie brilliant blue R-250. The result is shown in FIG. 7. In this figure, lane M is for a molecular weight marker of BRL Co., lanes 1–6 are for PROT-ABI to VI according to the present invention, and lane 7 is for a mixture of PROT-ABI to VI. Each marker protein clearly showed that they had the desired specific molecular weights.

EXAMPLE 5

Figure 8:
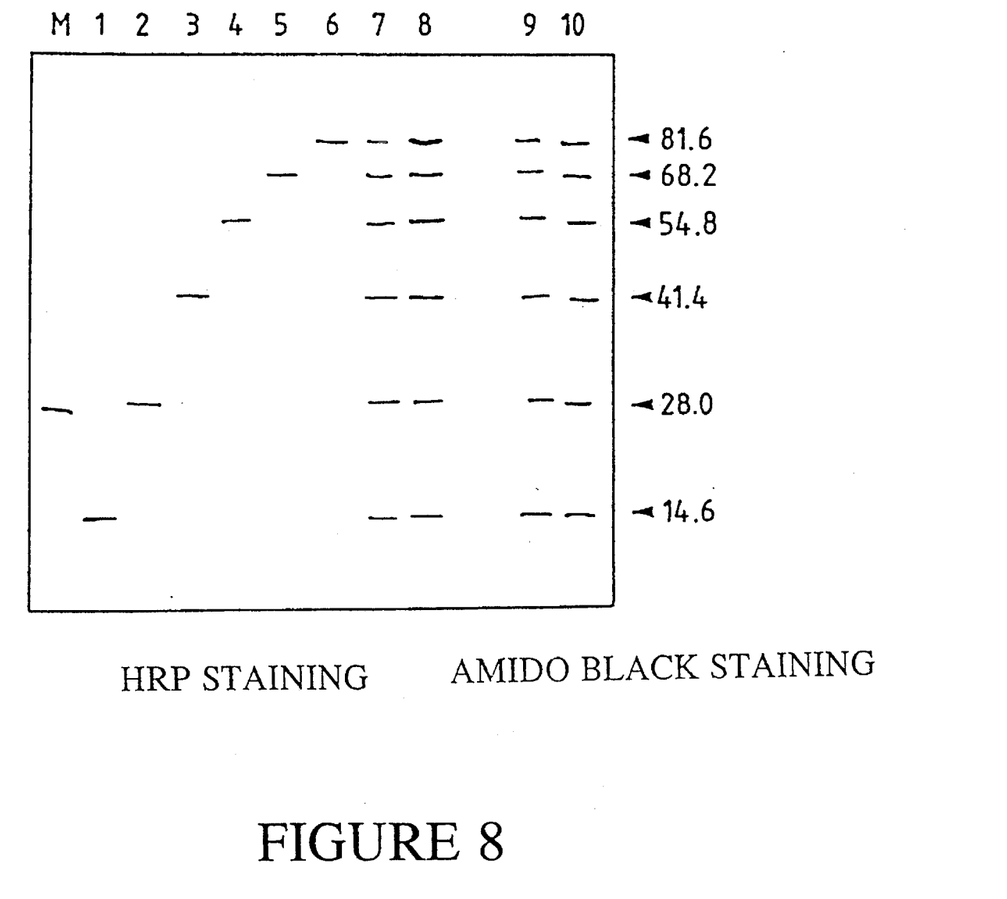

Each of the marker proteins were subjected to SDS-polyacrylamide gel electrophoresis in the same manner as desribed above, and were then electroblotted on a polyviniliden difluoride membrane. Rabbit IgG non-specific for the marker protein was bounded to each marker protein as the primary antibody, and then HRP-conjugated goat anti-rabbit antibody as the secondary antibody, and color development was carried out with 4-chloro-1-naphtol. The results obtained are shown in FIG. 8, with each lane corresponding to each of the lanes in FIG. 7. FIG. 8 clearly substantiates the fact that the molecular weight marker proteins (lanes 1–6) according to the present invention can also adequately function as molecular weight markers for immunoblotting. Lanes 7, 8, 9 and 10 show mixtures of PROT-ABI to VI, and lanes 9 and 10 are stained with Amido Black.

EXAMPLE 6

Each of the marker proteins produced in Example 3 when the D domain was defined as a repeating unit are used as molecular weight markers.

According to the present invention, each of the marker proteins of varying molecular weights are produced as desired. Protein A also has IgG-dinding domains, E and C (whose amino acid sequences are listed in FIG. 1), in addition to the above mentioned domains A, B and D. Thus, the same methods mentioned above may be used in the case of domains E and C as well, to easily produce the desired repetitive proteins between identical or different domains, and thus obtained repetitive proteins may be used for excellent molecular weight markers.

EFFECTS OF THE INVENTION

The present invention is directed to prepare an immunoglobulin-binding artificial protein with an excellent ability to purify IgG using genetic engineering techniques. It is possible to industrially produce the object repetitive proteins having exact molecular weights with ease, some of which exhibit an ability to separate and purify IgG in a more excellent manner than native protein A.

Thus, using the repetitive proteins in the present invention it is possible to efficiently separate and purify IgG, which plays an important role in all fields of biotechnology, and an efficient method is therefore provided for producing it in a highly pure form. Further, using the repetitive proteins in the present invention, IgG may be selectively isolated and removed from a sample, and thus the repetitive proteins may be used for exact and convenient bioassays of IgG in a sample.

In addition, the present invention produces marker proteins using genetic engineering techniques. It is possible to easily produce the object marker proteins each having an exact molecular weight by repeating some IgG-binding domain.

Thus, the molecular weight markers for western blotting obtained according to the present invention may be widely used not only for immunostaining methods, but also as general molecular weight markers, for SDS-polyacrylamide gel electrophoresis.

References to the microorganism deposited under Rule 13.2
1. *Escherichia coli* JM109/pTRP-PROT-AB 44

(a) Name and Address of the depository with which said microorganism is deposited.

Name: Fermentation Research Institute, Agency of Industrial Science and Technology, Ministry of International Trade and Industry Address: 1–3, Higashi 1 chome, Tsukuba-shi, Ibarakiken 305, Japan (b) Date deposited with the depository in (a): Jul. 15, 1992

(c) Deposit Receipt No. (Accession No.) assigned to the deposit with the depository in (a): FERM BP-3930.

---

We claim:

1. A method of using a mixture of immunoglobulin (Ig)-binding artificial proteins as molecular weight markers, comprising the steps of:

separating a mixture of at least two immunoglobulin-binding artificial proteins by SDS-polyacrylamide electrophoresis, said at least two immunoglobulin-binding proteins having different molecular weights, wherein each of said immunoglobulin-binding proteins comprises one or more iterations of an immunoglobulin-binding unit comprising one or more IgG-binding domains selected from the group consisting of domains A, B, C, D, and E of protein A;

electroblotting said separated immunoglobulin-binding artificial proteins onto a membrane;

reacting said proteins with an antibody, whereby said antibody binds to said proteins; and detecting the binding of said antibody to said proteins.

2. A method according to claim 1, wherein said immunoglobulin-binding unit comprises IgG-binding domains A and B of protein A.

3. A method according to claim 1, wherein said antibody is not specific for said immunoglobulin-binding artificial proteins.

4. A method according to claim 1, wherein said detecting comprises the steps of:

reacting said bound antibody with an enzyme-labeled secondary antibody, whereby said secondary antibody binds to said bound antibody;

adding a chromogenic substrate of said enzyme; and detecting the product formed by the action of said enzyme on said substrate.

5. A method of using an immunoglobulin (Ig)-binding artificial protein as a molecular weight marker, comprising the steps of:

subjecting an immunoglobulin-binding artificial protein to resolution by SDS-polyacrylamide electrophoresis, wherein said immunoglobulin-binding protein consists of one or more iterations of an immunoglobulin-binding unit, said unit consisting of one or more IgG-binding domains independently selected from the group consisting of domains A, C, D, and E of protein A;

electroblotting said resolved immunoglobulin-binding artificial protein onto a membrane;

reacting said protein with an antibody, whereby said antibody binds to said protein; and detecting the binding of said antibody to said protein.

6. A method according to claim 5, wherein said antibody is not specific for said immunoglobulin-binding artificial protein.

7. A method according to claim 5, wherein said detecting comprises the steps of:

reacting said bound antibody with an enzyme-labeled secondary antibody, whereby said secondary antibody binds to said bound antibody;

adding a chromogenic substrate of said enzyme; and detecting the product formed by the action of said enzyme on said substrate.

8. A method of using an immunoglobulin (Ig)-binding artificial protein as a molecular weight marker, comprising the steps of:

subjecting an immunoglobulin-binding artificial protein to resolution by SDS-polyacrylamide electrophoresis, wherein said immunoglobulin-binding protein consists of one or more iterations of an immunoglobulin-binding unit, said unit consisting of domains A and B of protein A;

electroblotting said resolved immunoglobulin-binding artificial protein onto a membrane;

reacting said protein with an antibody, whereby said antibody binds to said protein; and detecting the binding of said antibody to said protein.

9. A method according to claim 8, wherein said antibody is not specific for said immunoglobulin-binding artificial protein.

10. A method according to claim 8, wherein said detecting comprises the steps of:

reacting said bound antibody with an enzyme-labeled secondary antibody, whereby said secondary antibody binds to said bound antibody;

adding a chromogenic substrate of said enzyme; and detecting the product formed by the action of said enzyme on said substrate.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Thr Gly Arg Arg Phe Thr Thr Ser
1               5
```

( 2 ) INFORMATION FOR SEQ ID NO:2:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Ala Asp Ala Gln Gln Asn Asn Phe Asn Lys Asp Gln Gln Ser Ala Phe
1               5                   10                  15

Tyr Gln Ile Leu Asn Met Pro Asn Leu Asn Glu Ala Gln Arg Asn Gly
                20                  25                  30

Phe Ile Gln Ser Leu Lys Asp Asp Pro Ser Gln Ser Thr Asn Val Leu
                35              40                  45

Gly Glu Ala Lys Lys Leu Asn Glu Ser Gln Ala Pro Lys
            50              55                  60
```

( 2 ) INFORMATION FOR SEQ ID NO:3:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:3:

```
Ala Asp Asn Asn Phe Asn Lys Glu Gln Gln Asn Ala Phe Tyr Gln Ile
1               5                   10                  15

Leu Asn Met Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ser Glu Ala
            35              40                  45

Lys Lys Leu Asn Glu Ser Gln Ala Pro Lys
            50              55
```

( 2 ) INFORMATION FOR SEQ ID NO:4:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:4:

```
Ala Asp Asn Lys Phe Asn Lys Glu Gln Gln Asn Ala Phe Tyr Gln Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35              40                  45

Lys Lys Leu Asn Asp Ala Gln Ala Pro Lys
            50              55
```

( 2 ) INFORMATION FOR SEQ ID NO:5:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:5:

```
Ala  Asp  Asn  Lys  Phe  Asn  Lys  Glu  Gln  Gln  Asn  Ala  Phe  Tyr  Gln  Ile
 1              5                        10                       15

Leu  His  Leu  Pro  Asn  Leu  Thr  Glu  Glu  Gln  Arg  Asn  Gly  Phe  Ile  Gln
              20                       25                       30

Ser  Leu  Lys  Asp  Asp  Pro  Ser  Val  Ser  Lys  Glu  Ile  Leu  Ala  Glu  Ala
              35                       40                       45

Lys  Lys  Leu  Asn  Asp  Ala  Gln  Ala  Pro  Lys
              50                       55
```

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

GGTAGACGCT GATAACAATT TCAACAAA             28

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

GGTCTACTTT TGGTGCTTGA GCATCATTTA            30

( 2 ) INFORMATION FOR SEQ ID NO:8:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:8:

GGAATTCATG AAAGTAGACA CTGGCCGTCG TTTTACAA          38

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA (genomic)

(  x i  ) SEQUENCE DESCRIPTION: SEQ ID NO:9:

GGAATTCTAC CCTTTTTACG T                                                                21

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:10:

Met Lys Val Asp
1

( 2 ) INFORMATION FOR SEQ ID NO:11:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:11:

Ala Gln His Asp Glu Ala Gln Gln Asn Ala Phe Tyr Gln Val Leu Asn
1           5               10                  15

Met Pro Asn Leu Asn Ala Asp Gln Arg Asn Gly Phe Ile Gln Ser Leu
            20              25                  30

Lys Asp Asp Pro Ser Gln Ser Ala Asn Val Leu Gly Glu Ala Gln Lys
        35              40                  45

Leu Asn Asp Ser Gln Ala Pro Lys
    50              55